Figure 1:
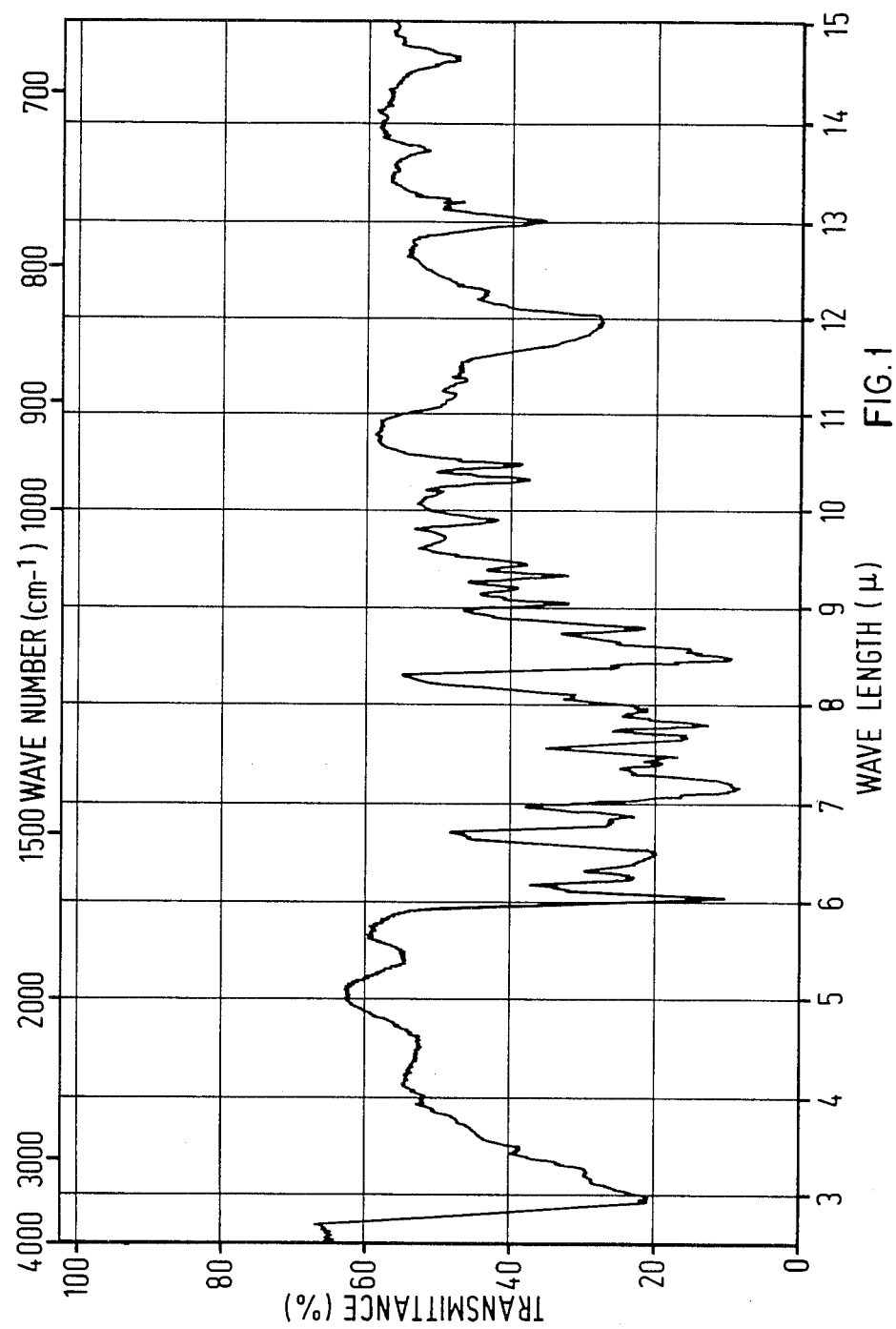

United States Patent [19]

Bhat et al.

[11] Patent Number: 4,603,137

[45] Date of Patent: Jul. 29, 1986

[54] IMMUNOSUPPRESSIVE CHROMONE ALKALOID

[75] Inventors: Sujata V. Bhat, Thane; Virbala Shah, Bombay; Alihussein N. Dohadwalla, Bombay; Sadashiv M. Mandrekar, Bombay; Noel J. de Souza, Bombay, all of India; Gerhard Dickneite, Marburg-Cappel, Fed. Rep. of Germany; Roland Kurrle, Marburg, Fed. Rep. of Germany; Hans-Ulrich Schorlemmer, Weimar, Fed. Rep. of Germany; Hans-Harald Sedlacek, Marburg, Fed. Rep. of Germany

[73] Assignee: Hoechst Aktiengesellschaft, Fed. Rep. of Germany

[21] Appl. No.: 639,312

[22] Filed: Aug. 10, 1984

[30] Foreign Application Priority Data

Aug. 12, 1983 [DE] Fed. Rep. of Germany ....... 3329186

[51] Int. Cl.[4] ................ A61K 31/445; C07D 405/04
[52] U.S. Cl. ................................ 514/320; 424/195.1; 546/196
[58] Field of Search ............... 546/196; 514/320, 314; 424/195.1

[56] References Cited

U.S. PATENT DOCUMENTS 3,484,445 12/1969 Lee et al. ........................... 260/294

OTHER PUBLICATIONS

Alan D. Harmon, Ulrich Weiss, and J. V. Silverton, *Tetrahedron Letters*, 721-724 (1979).

*Primary Examiner*—Richard A. Schwartz
*Attorney, Agent, or Firm*—Finnegan, Henderson, Farabow, Garrett & Dunner

[57] ABSTRACT

The present invention relates to a compound of the formula

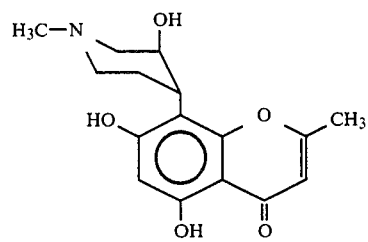

and to a process for its isolation from plants of the family comprising the meliaceae. The compound has, in particular, immunosuppressive properties, and can therefore be used as a medicament.

2 Claims, 5 Drawing Figures

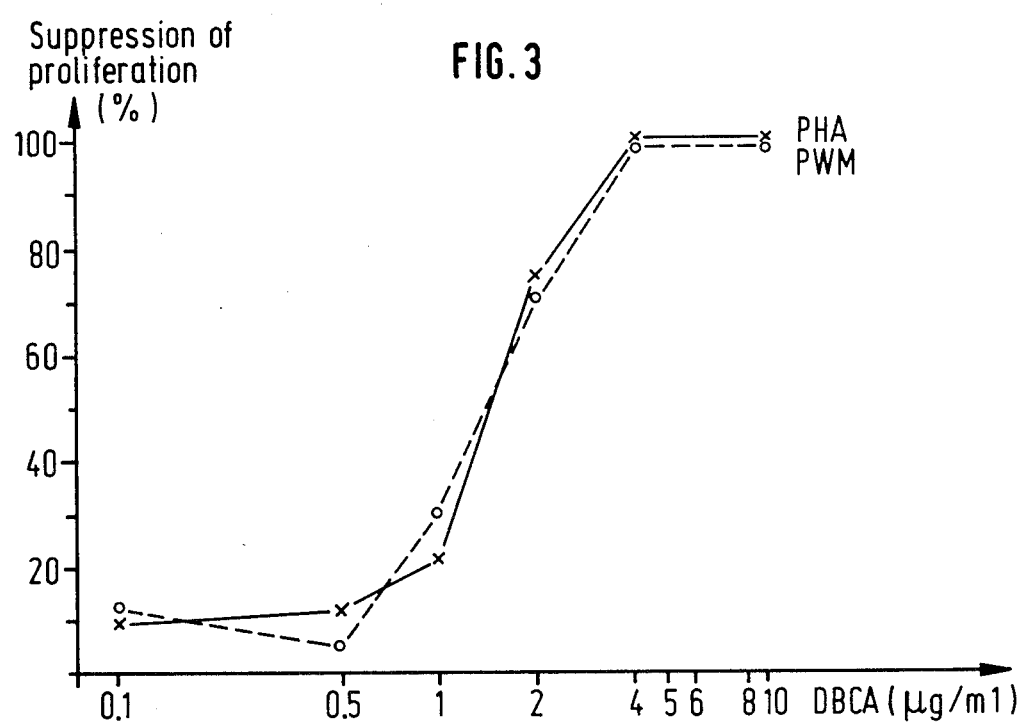

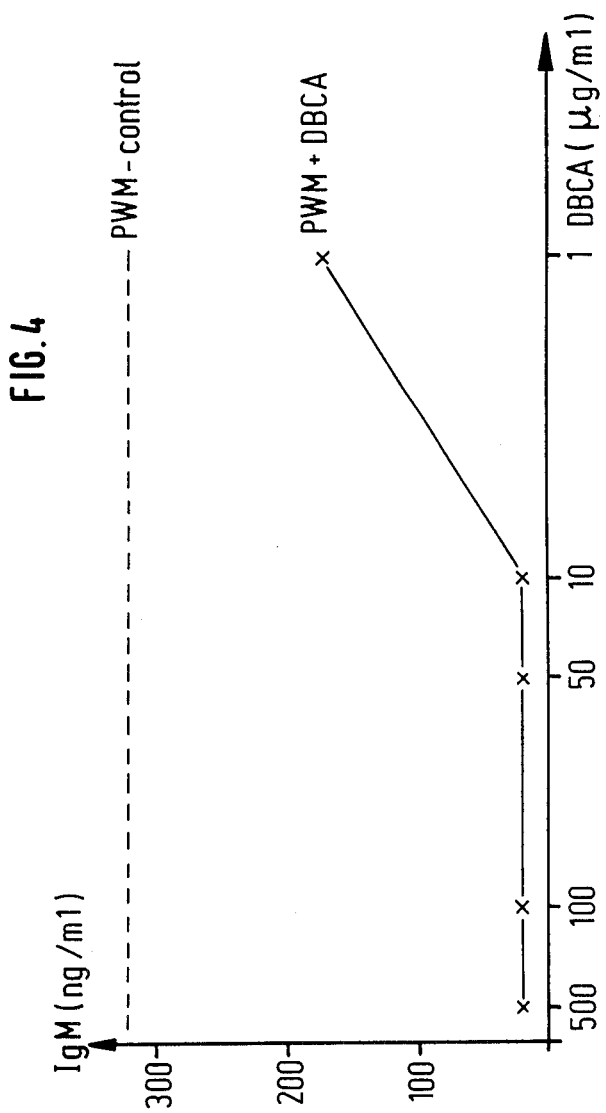

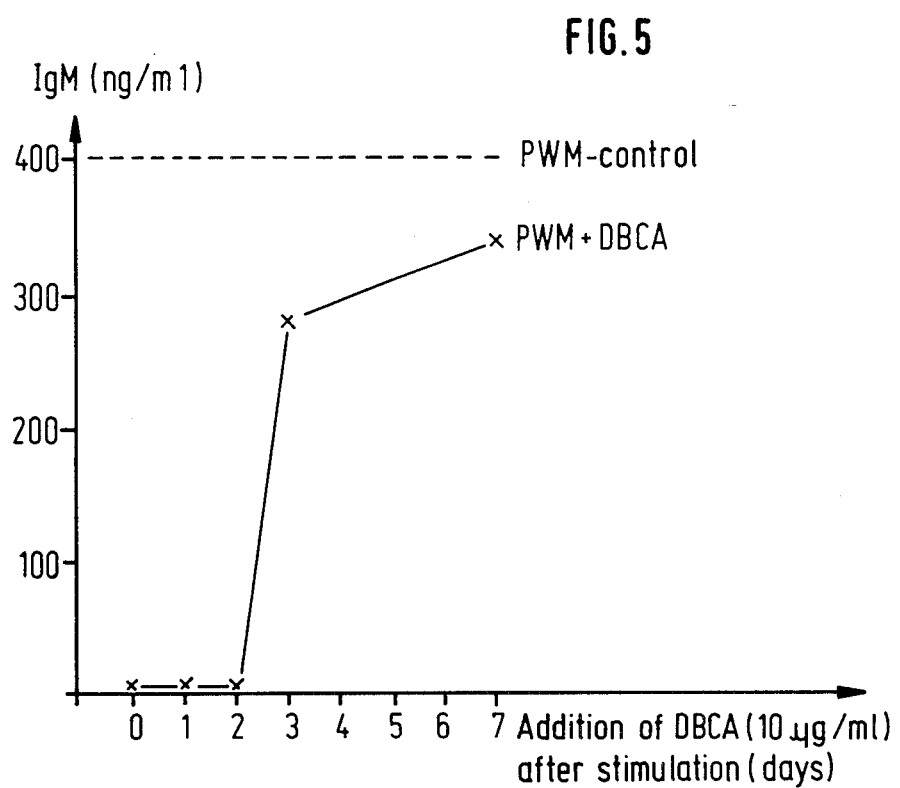

IMMUNOSUPPRESSIVE CHROMONE ALKALOID

The present invention relates to a pharmacologically active substance which can be isolated from a plant belonging to the family of the meliaceae, in particular the plant *Dysoxylum binectariferum*. The invention furthermore relates to a process for isolating this substance from *Dysoxylum binectariferum*, if appropriate in the form of the free base or its salts.

The family of the meliaceae comprises about 550 species of plants, distributed over 50 genera. Of these species, Dysoxylum, Chisocheton, Sandoricum, Aglaia, Lansium, Amoora, Walsura, Heynea, Beddomea and Xylocarpus grow in India. The morphological details and the classification of these species are described in Hooker "Flora of British India", Vol. I, pages 540–569.

The pharmacologically active substance according to the invention was isolated from various parts of the plant *Dysoxylum binectariferum*, i.e. leaves, branches, bark and wood of the trunk, and bark and wood of the roots.

The invention relates to a pharmacologically active substance having the structure of a chromone alkaloid of the formula I

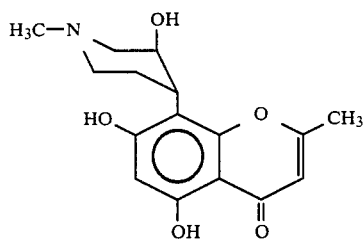

and to a process for isolating this substance from plants of the family comprising the meliaceae.

In the process, the dried and ground plant material is first extracted with a lower alkanol and, if required, then with a lower alkanol/alkali metal hydroxide mixture and a lower alkanol/acetic acid mixture, after which the combined extracts are treated as described below in order to obtain the pharmcologically active alkaloid, and, if required, the alkaloid is converted to the pharmaceutically acceptable salts in a conventional manner by treatment with acids.

It is advantageous to use various parts of the plant *Dysoxylum binectariferum*, such as leaves, branches, bark and wood of the trunk or of the roots, in particular the bark of the trunk in the form of a dried and ground powder.

To extract the active substance from *Dysoxylum binectariferum*, it is possible to use an organic solvent, such as methanol, ethanol, isopropanol or any other lower alcohol, methanol being preferred. The volume of alkanol used for the extraction is preferably in the ratio 1:5 (parts by weight of plant material to alkanol). Methanolic sodium hydroxide solution (900 ml of methanol+100 ml of NaOH) and subsequently methanolic acetic acid (900 ml of methanol+100 ml of 1% strength acetic acid) are used for the extraction in the same ratio. The methanolic extracts are combined, brought to pH 2 with hydrochloric acid and extracted with chloroform. The extract is discarded. The acidic solution is then brought to pH 8 with aqueous sodium hydroxide solution (1N), and the resulting solution is freeze-dried. This gives a solid residue, which is dissolved in methanol, and the methanol solution is filtered and evaporated down, and the residue is then allowed to crystallize. Recrystallization from aqueous acetone gives a crystalline product of melting point 229°–232° C., which constitutes the pharmacologically active free base according to the invention.

This free base can, if required, then be converted to acid salts by treatment with inorganic and organic acids, such as hydrochloric acid, nicotinic acid, maleic acid and methanesulfonic acid, or by treatment with ammonium salts, such as ammonium thiocyanate.

Figure 2:
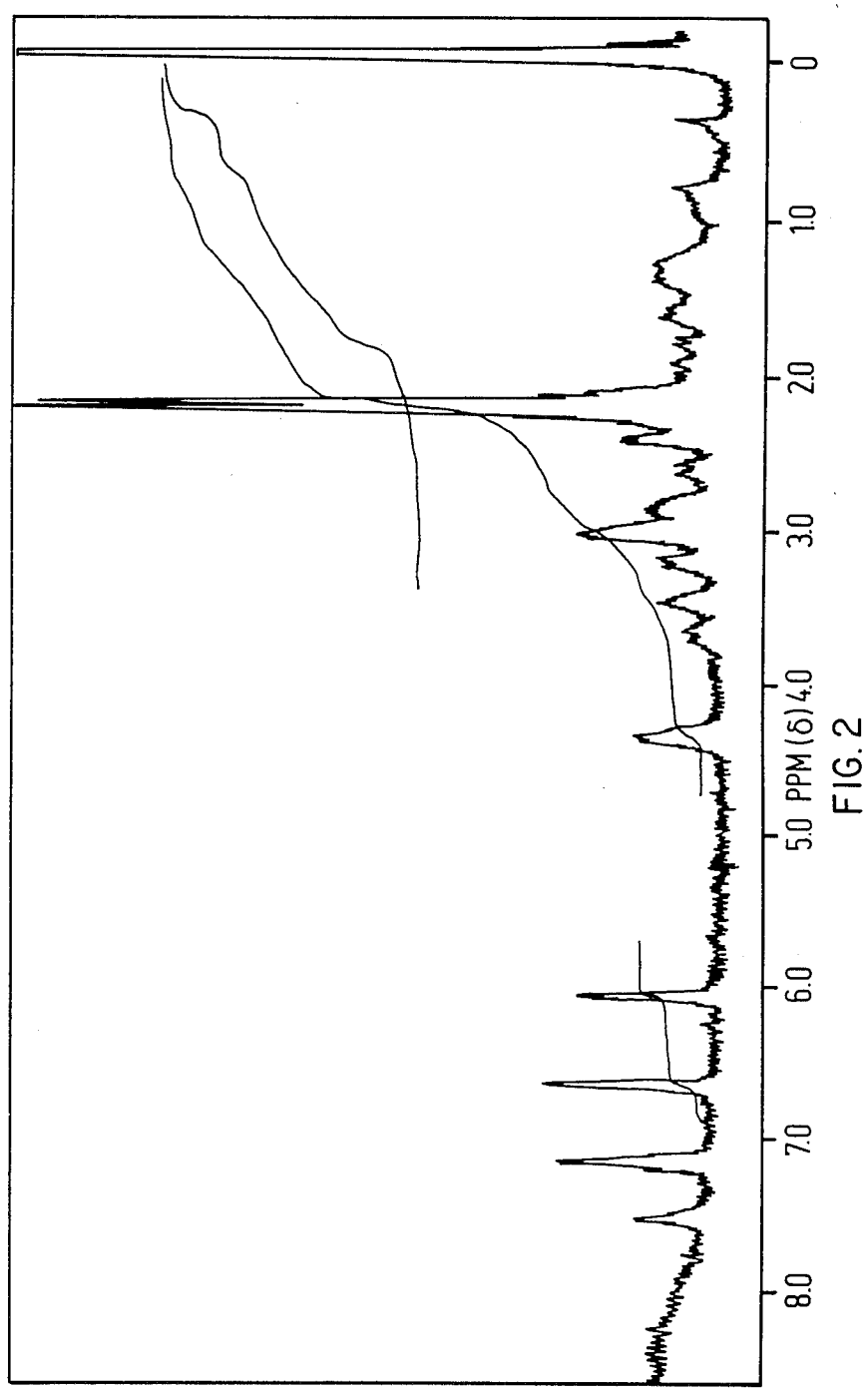

The empirical formula of the free base is $C_{16}H_{19}NO_5$, calculated from the molecular weight of 305 units of mass (determined from the mass spectrum) and from elemental analysis. The UV spectrum in methanol shows absorption at $\lambda_{max}$ 210, 228, 266 and 326 nm. The IR spectrum was measured on KBr pellets, and the NMR spectrum with deuterated pyridine. FIGS. 1 and 2 show, respectively, the IR spectrum and the NMR spectrum.

The specific rotation $[\alpha]_D^{25}$ measured in methanol has the value +44.31 (c: 13 mg/ml in methanol).

The various acid addition salts prepared from the free base are listed below:

| Salt | Molecular formula | m.p. °C. |
|---|---|---|
| Hydrochloride | $C_{16}H_{20}ClNO_5 \cdot \frac{1}{2} H_2O$ | 228–243 |
| Nicotinate | $C_{22}H_{24}N_2O_7 \cdot \frac{1}{2} H_2O$ | 188–190 |
| Maleate | $C_{20}H_{23}NO_9$ | 186–188 |
| Methanesulfonate | $C_{17}H_{23}NO_8S \cdot \frac{1}{2} H_2O$ | 222–224 |
| Thiocyanate | $C_{17}H_{20}N_2O_5S$ | 224–228 |

The pharmacologically active free base possesses chemical and physical properties usually found in the case of chromones and alkaloids. All physical and chemical data confirm the chromone alkaloid structure attributed to the free base. The literature (A. D. Harmon, V. Weiss and J. V. Silverton, Tetrahedron Letters, 721 (1979)) mentions a compound called rohitukine, which has the same empirical formula and is said to have been isolated from the plant *Amoora rohituka*. The data available to date is insufficient for determining whether there are stereochemical differences between rohitukine and the compound according to the invention.

The above pharmacologically active chromone alkaloid and its acid addition salts are distinguished by very good antiinflammatory, analgesic and immunomodulatory properties in laboratory animals and in in vitro experiments.

The chromone alkaloid according to the invention can be used, in particular, in the treatment of patients having undesirable responses of the immune system, present in the case of autoimmune diseases, which as a rule are caused by antibodies, and of hyperergic or allergic conditions of the organism, and in the case of chronic inflammatory responses, the principal contributors to which are macrophages and granulocytes. The chromone alkaloid can furthermore be used as an immunosuppressive agent for preventing rejection or organ transplants, lymphocytes and macrophages playing an important role in this prevention.

The Examples which follow are intended to illustrate the invention in more detail.

EXAMPLE 1

The dried and ground bark of the trunk of *Dysoxylum binectariferum* (24 kg) is extracted with three times 50 l of methanol, then with three times 50 l of methanol/-sodium hydroxide solution (900 ml of methanol+100 ml of 0.1N NaOH) and then with three times 50 l of methanol/acetic acid (900 ml of methanol+100 ml of 1% strength acetic acid). The combined methanol extracts are brought to pH 2 with hydrochloric acid, and the solution is extracted with chloroform. The chloroform extract is discarded, and the acidic solution is brought to pH 8 with aqueous sodium hydroxide solution (1N). The basic solution is then freeze-dried, and gives a solid residue (475 g), which is treated with 7 l of methanol and filtered. The filtrate is evaporated down, and the residue is brought to crystallization. The crystals obtained are filtered (415 g) and are recrystallized from aqueous acetone. In this manner, the pharmacologically active alkaloid according to the invention (300 g) of melting point 229°–232° C. is obtained.

EXAMPLE 2

The substance of melting point 229°–232° C. was obtained in the same manner as in Example 1, except with the use of dried and ground root bark instead of the bark of the trunk.

EXAMPLE 3 (NICOTINATE SALT)

The active base from Example 1 was dissolved in methanol, the solution was treated with an equivalent amount of nicotinic acid solution in methanol, and the mixture was evaporated to dryness. A solid residue was obtained which, when recrystallized from methanol-/ethyl acetate, gave the nicotinate salt of melting point 188°–190° C.

EXAMPLE 4 (MALEATE SALT)

The maleate salt of melting point 186°–188° C. (methanol/ethyl acetate) was obtained analogously to the procedure of Example 3, but with the use of maleic acid instead of nicotinic acid.

EXAMPLE 5 (METHANESULFONATE SALT)

The methanesulfonate salt of melting point 222°–224° C. (methanol/ethyl acetate) was obtained analogously to the procedure of Example 3, except with the use of methanesulfonic acid instead of nicotinic acid.

EXAMPLE 6 (HYDROCHLORIDE SALT)

The hydrochloride of melting point 228°–234° C. (water/acetone) was obtained analogously to the procedure of Example 3, except with the use of hydrochloric acid instead of nicotinic acid.

EXAMPLE 7 (THIOCYANATE SALT)

The thiocyanate of melting point 224°–228° C. (methanol/ethyl acetate) was obtained analogously to the procedure of Example 3, except with the use of ammonium thiocyanate instead of nicotinic acid.

The model for demonstrating the immunosuppressive potency of the substance according to the invention (abbreviated below to DBCA) comprised tests for determining the action of lymphocytes, macrophages and granulocytes in vitro, and the humoral immunity, measured as the antibody response to a range of antigens (thymus-dependent and thymus-independent antigens) in vivo.

The model described here was specially chosen to characterize the immunosuppressive potency of this substance.

ACTION OF DBCA ON THE HUMORAL IMMUNE RESPONSE

Test 1: Action on the antibody response to sheep erythrocytes in vivo (thymus-dependent antigen).

Female NMRI mice were immunized intravenously with $10^6$ sheep erythrocytes. At the same time, DBCA was administered intravenously in concentrations of 5, 10, 20 or 50 mg/kg. The control group received, as the solvent, physiologically buffered saline solution (PBS). After six days, the serum level of lysing and agglutinating antibodies against sheep erythrocytes was determined. As shown in Table 1, the titer of lysing and of agglutinating antibodies was lowered by the substance according to the invention.

TABLE 1

| Action of DBCA on the antibody response to sheep erythrocytes in vivo | | |
|---|---|---|
| | Agglutinating antibodies | Lysing antibodies |
| Control | 7.6 ± 0.9 | 6.6 ± 0.9 |
| 5 mg/kg i.v. | 5.8 ± 1.3 | 4.0 ± 1.6 |
| 10 mg/kg i.v. | 5.6 ± 0.5 | 4.6 ± 1.3 |
| 20 mg/kg i.v. | 5.4 ± 0.5 | 3.6 ± 0.5 |
| 50 mg/kg i.v. | 4.6 ± 1.3 | 3.0 ± 1.2 |

Test 2: Action on the IgM antibody response to *E. coli* killed organisms in vivo (thymus-independent antigen).

Female mice were immunized intravenously with $10^8$ heat-inactivated *E. coli* bacteria. DBCA was injected as described in Example 1. 10 days after the immunization, the IgM-class antibodies to *E. coli* were determined with the aid of the ELISA technique. As shown in FIG. 2, the administration of DBCA resulted in a pronounced decrease in the optical density ($E_{492\ nm}$), which is a measure of the antibody concentration.

TABLE 2

| Action of DBCA on the antibody response to *E. coli* killed organisms | |
|---|---|
| | $E_{492\ nm}$ (1:40) |
| Control | 1.528 ± 0.332 |
| 5 mg/kg i.v. | 0.402 ± 0.091 |
| 10 mg/kg i.v. | 0.262 ± 0.100 |
| 20 mg/kg i.v. | 0.228 ± 0.052 |
| 50 mg/kg i.v. | 0.179 ± 0.024 |

Test 3: Action of DBCA on the antibody response to human serum albumin (HSA) in vivo Female mice wee immunized intravenously with 100 μg of HSA. DBCA was injected as described in Example 1. 14 days later, the IgG-class antibodies to HSA were determined with the aid of the ELISA technique. Table 3 shows that the antibody response was suppressed by the substance according to the invention.

TABLE 3

| Action of DBCA on the immune response to HSA | |
|---|---|
| | $E_{492\ nm}$ (1:10) |
| Control | 0.336 ± 0.215 |
| 10 mg/kg i.v. | 0.194 ± 0.169 |
| 20 mg/kg i.v. | 0.126 ± 0.082 |
| 50 mg/kg i.v. | 0.138 ± 0.081 |
| 100 mg/kg i.v. | 0.175 ± 0.175 |

Test 4: Action on the antibody response to tetanus toxoid in vivo

Female NMRI mice were immunized intravenously with 300 Lf of tetanus toxoid. DBCA was injected as described in Example 1. 10 days later, the IgG-class antibodies to tetanus toxoid were determined with the aid of the ELISA technique. Table 4 shows the reduction in the antibody response as a result of DBCA.

TABLE 4

| Action of DBCA on the antibody response to tetanus toxoid | |
|---|---|
| | $E_{492\ nm}$ (1:10) |
| Control | 0.253 ± 0.163 |
| 5 mg/kg i.v. | 0.192 ± 0.168 |
| 10 mg/kg i.v. | 0.150 ± 0.068 |
| 20 mg/kg i.v. | 0.195 ± 0.046 |
| 50 mg/kg i.v. | 0.112 ± 0.026 |

Test 5: Action on the antibody-producing spleen cells in vitro.

Female NMRI mice were immunized intravenously with $10^8$ sheep erythrocytes. After 10 days, the spleens were removed and the isolated spleen cells were cultured in Costar plates ($5-8 \times 10^6$ cells per well). DBCA was added to the cultures, in concentrations of 0.1–10 μg/ml. After three days, the antibody-forming spleen lymphocytes (IgG, IgM) were determined by the plaque-forming cell test according to Jerne. Table 5 shows that both the IgG-secreting and the IgM-secreting spleen lymphocytes were suppressed.

TABLE 5

| Action of DBCA on the antibody-secreting spleen lymphocytes | | |
|---|---|---|
| | Plaque forming cells IgG | $10^6$ spleen lymphocytes IgM |
| Control | 1949 ± 971 | 1716 ± 870 |
| 0.1 μg/ml | 1665 ± 1056 | 1323 ± 164 |
| 0.5 μg/ml | 842 ± 281 | 1912 ± 1041 |
| 0.75 μg/ml | 367 ± 162 | 859 ± 396 |
| 1.0 μg/ml | 197 ± 166 | 1128 ± 452 |
| 2.5 μg/ml | ∅ ∅ | 289 ± 68 |
| 5.0 μg/ml | ∅ ∅ | ∅ ∅ |
| 10.0 μg/ml | ∅ ∅ | ∅ ∅ |

Test 6: Effect of DBCA on the stimulation of murine and human phagocytes.

Mononuclear phagocytes and neutrophilic granulocytes from peripheral blood of healthy donors and mouse peritoneal macrophages were obtained, and were tested for various functions after the preparation had been administered. The chemiluminescence reaction and the secretion of lysosomal enzymes were investigated, as parameters of the phagocyte function.

Compared with phagocytes of the corresponding control groups (untreated cells), the chemiluminescence reaction both in the case of mouse macrophages and in the case of human phagocytes (monocytes and granuloctyes) exhibited a significant dose-dependent (40–400 μg/ml) decrease (see Table 6a). This suppressive action of DBCA is even more pronounced in the case of costimulation with zymosan (100 μg/ml).

Mouse peritoneal macrophages treated with the substance are also distinguished in particular by the fact that their secretion of lysosomal enzymes is substantially inhibited (Table 6b).

TABLE 6a

| Oxidative metabolism (chemiluminescence) with and without zymosan (100 μg/ml) | | | |
|---|---|---|---|
| | DBCA | Integral of the RW/15 min ($\times 10^3$) | |
| Cell type | μg/ml | −zymosan | +zymosan |
| Mouse macrophages | 0 | 1185 ± 49 | 4686 ± 275 |
| | 50 | 1097 ± 23 | 3835 ± 195 |
| | 100 | 874 ± 31 | 2047 ± 147 |
| | 200 | 523 ± 46 | 1175 ± 35 |
| | 400 | 345 ± 38 | 571 ± 29 |
| Human monocytes | 0 | 2130 ± 71 | 6365 ± 189 |
| | 50 | 1905 ± 149 | 5832 ± 162 |
| | 100 | 1511 ± 32 | 4221 ± 157 |
| | 200 | 955 ± 78 | 2668 ± 74 |
| | 400 | 434 ± 43 | 1235 ± 49 |
| Human granulocytes | 0 | 3142 ± 127 | 9389 ± 217 |
| | 50 | 2897 ± 276 | 7551 ± 458 |
| | 100 | 1927 ± 152 | 5004 ± 191 |
| | 200 | 864 ± 66 | 1997 ± 107 |
| | 400 | 248 ± 15 | 542 ± 38 |

TABLE 6b

| Effect of the test substance on the enzymatic liberation of lysosomal hydrolases of mouse peritoneal macrophages. | | | |
|---|---|---|---|
| Substance μ/ml | β-Glu mU/ml | β-Gal mU/ml | β-Ac—Glu mU/ml |
| 0 | 1956 ± 108 | 16295 ± 327 | 5521 ± 264 |
| 50 | 1793 ± 125 | 13596 ± 272 | 4676 ± 182 |
| 100 | 1197 ± 69 | 9058 ± 148 | 2872 ± 159 |
| 200 | 736 ± 23 | 4584 ± 186 | 1749 ± 65 |
| 400 | 348 ± 30 | 1731 ± 102 | 1128 ± 38 |

Test 7: Effect of DBCA on the mitogen-induced lymphocyte proliferation (human).

It is known that phytohemagglutinin (PHA), which is a T-cell mitogen, and pokeweed mitogen (PWM), which is a T-cell-dependent B-cell mitogen, stimulate human peripheral lymphocytes to polyclonal differentiation and proliferation. The effectiveness of the lymphocyte activation is measured via the incorporation of $^{14}$C-thymidine. On day 0 (beginning of culture), various concentrations (0.1–500 μg/ml) of DBCA were added to human lymphocytes, which, in a proliferation test of this type, were stimulated with the mitogens PHA or PWM, and the amount of $^{14}$C-thymidine incorporated was measured after 3 days. The results shown by way of example in FIG. 3 show that donor-dependent DBCA concentrations of >4 μg/ml completely inhibit both the PHA-induced and the PWM-induced lymphocyte transformation. This effect cannot be attributed to a non-specific toxicity, since DBCA in a concentration of 1 mg/ml (incubation for 24 hours) is non-toxic to human lymphocytes (vital staining).

Further proliferation experiments showed that DBCA can have an inhibitory effect even when lymphocyte activation is complete.

Test 8: Effect of DBCA on the PWM-induced in vitro IgM synthesis (human).

The activation of the cellular components of the immune system during an immune reaction can in principle be divided into the stages of induction, proliferation, differentiation and effector performance. In order to test whether DBCA, in addition to having suppressive inhibitory effects in the induction phase and proliferation phase (see Example 7), also has these effects on the effector phase of an immune reaction, DBCA was added in various concentrations (0.1–500 μg/ml) to PWM-stimulated lymphocyte cultures.

The results presented in FIG. 4 show that, depending on the lymphocyte donor, DBCA concentrations of >10 µg/ml completely suppress the in vitro-induced IgM-synthesis. If DBCA is added, in a concentration of >10 µg/ml, to a culture system of this type on various days after induction of the IgM synthesis (measurement of the amount of IgM on day 9), DBCA is found to have a suppressive action on the induction phase and proliferation phase of the lymphocyte activation, as shown in FIG. 5.

We claim:

1. A method for the treatment of a patient having undesirable response of the immune system, hyperergic or allergic conditions or chronic inflammatory responses, which comprises administering to said patient a pharmaceutically effective amount of a compound of the formula I or a physiologically acceptable acid addition salt thereof.

2. A pharmaceutical composition comprising compound of the formula I or a physiologically acceptable acid addition salt therefor in combination with a pharmaceutically acceptable carrier, said compound or salt thereof being present in an amount sufficient to act as an immunosuppressive agent.

* * * * *